(12) United States Patent
Niu et al.

(10) Patent No.: US 11,608,482 B2
(45) Date of Patent: Mar. 21, 2023

(54) DEVICE FOR PRODUCING BIOGAS WITH HIGH METHANE CONTENT BY UTILIZING LIVESTOCK AND POULTRY FECES

(71) Applicants: SOUTH CHINA UNIVERSITY OF TECHNOLOGY, Guangdong (CN); GUANGDONG UNIVERSITY OF PETROCHEMICAL TECHNOLOGY, Guangdong (CN); GUANGZHOU INSTITUTE OF ENERGY CONVERSION, CHINESE ACADEMY OF SCIENCES, Guangzhou (CN)

(72) Inventors: XiaoJun Niu, Guangdong (CN); MengYu Lv, Guangdong (CN); Xia Li, Guangdong (CN); Li Zhang, Guangdong (CN); NingYu Tu, Guangdong (CN); XingYao Ye, Guangdong (CN); DongQing Zhang, Guangdong (CN); LiHua Cheng, Guangdong (CN); HuaFang Guo, Guangzhou (CN)

(73) Assignees: South China University of Technology, Guangdong (CN); Guangdong University of Petrochemical Technology, Guangdong (CN); Guangzhou Institute of Energy Conversion, Chinese Academy of Sciences, Guangzhou (CN)

( * ) Notice: Subject to any disclaimer, the term of this patent is extended or adjusted under 35 U.S.C. 154(b) by 442 days.

(21) Appl. No.: 16/746,253

(22) Filed: Jan. 17, 2020

(65) Prior Publication Data
US 2021/0139826 A1  May 13, 2021

(30) Foreign Application Priority Data
Nov. 8, 2019  (CN) .......................... 201911088918.5

(51) Int. Cl.
*C12M 1/107* (2006.01)
*C05F 17/50* (2020.01)
(Continued)

(52) U.S. Cl.
CPC .............. *C12M 21/04* (2013.01); *C02F 11/04* (2013.01); *C05F 17/50* (2020.01); *C12M 23/36* (2013.01); *C02F 2103/20* (2013.01); *C12M 41/24* (2013.01)

(58) Field of Classification Search
CPC ...... C12M 21/04; C12M 23/36; C12M 41/24; C05F 17/50; C02F 11/04; C02F 2103/20; A01C 3/023; A01C 3/028; B01D 2258/05
See application file for complete search history.

(56) References Cited

U.S. PATENT DOCUMENTS 5,525,229 A * 6/1996 Shih ....................... C12M 45/20
 210/603
6,299,774 B1 * 10/2001 Ainsworth ............. C12M 47/20
 210/603

(Continued)

*Primary Examiner* — William H. Beisner
*Assistant Examiner* — Danielle B Henkel
(74) *Attorney, Agent, or Firm* — Juan Carlos A. Marquez; Marquez IP Law Office, PLLC

(57) ABSTRACT

The invention discloses a device for producing biogas with high methane content by utilizing livestock and poultry feces, wherein the interior of a tank body of a biogas fermentation tank is divided by a baffle, so as to form a main reaction chamber and an auxiliary reaction chamber which are communicated in upper portions, so that a reactant flows into the auxiliary reaction chamber only after entering the main reaction chamber via a relatively low feeding hole and then reaching a high position of a liquid level, and extension of fermentation time is realized, meanwhile, scales formed at the top of fermentation broth flow into the auxiliary reaction chamber along with liquid, so that the interior of the main reaction chamber keeps a liquid state all the time, and (Continued)

sealing and reduction of quantity of anaerobic bacteria are avoided.

4 Claims, 3 Drawing Sheets

(51) Int. Cl.
  *C02F 11/04* (2006.01)
  *C12M 1/02* (2006.01)
  *C02F 103/20* (2006.01)

(56) References Cited

U.S. PATENT DOCUMENTS

| | | | |
|---|---|---|---|
| 8,043,505 B2* | 10/2011 | Noguchi | C10L 5/46 |
| | | | 422/600 |
| 2004/0025715 A1* | 2/2004 | Bonde | C05F 17/50 |
| | | | 99/485 |
| 2007/0062866 A1* | 3/2007 | Wilson | C02F 3/286 |
| | | | 210/603 |
| 2011/0005393 A1* | 1/2011 | Howard | B01D 53/0438 |
| | | | 95/114 |
| 2016/0200607 A1* | 7/2016 | Gilron | C02F 3/1273 |
| | | | 210/151 |
| 2017/0240478 A1* | 8/2017 | Massai | C05G 5/23 |
| 2018/0346858 A1* | 12/2018 | Kim | C12M 39/00 |

* cited by examiner

DEVICE FOR PRODUCING BIOGAS WITH HIGH METHANE CONTENT BY UTILIZING LIVESTOCK AND POULTRY FECES

TECHNICAL FIELD

The invention relates to the technical field of virtual reality, and specifically relates to a device for producing biogas with high methane content by utilizing livestock and poultry feces.

BACKGROUND

Livestock and poultry feces take organic matters as main components, contain many plant nutritional ingredients including rich nitrogen, phosphorus, potassium, humus and the like, and may be made into high-quality and high-efficiency organic compound fertilizers by drying or fermenting, mould prevention, deodorization and sterilization; livestock and poultry feces may also produce biogas energy by an anaerobic fermentation treatment device, and the calorific value of biogas is 25675KJ/m on average, which is 0.65 time of the caloric value of diesel, and 1.12 times of the calorific value of raw coal. However, biogas prepared with an existing process of producing biogas with livestock and poultry is low in methane content, and low in heat supply efficiency, there is nearly no retreatment process for biogas slurry and biogas residue, biogas slurry and biogas residue are directly discharged and will cause pollution, meanwhile, and existing biogas production reaction tanks take CSTR as a main device, and easily produce scales, which reduces fermentation efficiency.

SUMMARY

The invention is directed to overcome the foregoing disadvantages of the prior art, and provides a device for producing biogas with high methane content by utilizing livestock and poultry feces, which produces biogas with high methane content by taking livestock and poultry feces as raw material.

In order to achieve the foregoing purpose, the invention provides the following technical scheme:

A device for producing biogas with high methane content by utilizing livestock and poultry feces, including:

a feces collecting pond used for collecting livestock and poultry feces in a unified mode, wherein the feces collecting pond is internally provided with grids for filtering feces; the feces collecting pond is used for collecting livestock and poultry feces in a unified mode, and may adopt general settings in the prior art, as for large-scale farms, collecting pipelines may be provided in the bottom of a livestock and poultry captive breeding area, so that feces of livestock and poultry and flushing sewage are automatically collected to the feces collecting pond via inclined pipelines, meanwhile, the feces collecting pond may also be used as transiting buffer, so as to be convenient for regular maintenance and be taken as a storage station when a subsequent device has fault temporarily; grids are used for intercepting large-size wastes, so as to prevent blockage of pipelines in a transportation process;

an acidifying pond connected with the feces collecting pond by a pipeline and used for acidifying livestock and poultry feces, wherein the acidifying pond is internally provided with an agitator, and externally provided with an automatic doser or dosing device; an acidifying process is that macrofibers in livestock and poultry feces are acidified to be simple organic matters to be convenient for subsequent anaerobic bacteria treatment, by utilizing an agitator, contact area between feces and an acidifier may be enlarged, acidolysis time is shortened, and acidolysis efficiency is increased, and a turbo type agitator, an anchor agitator or a propeller agitator applicable to high-thickness media may be adopted as an agitator, or a baffle may be provided on a wall of the pond to increase the mixing efficiency;

a biogas fermentor connected with the acidifying pond by a pipeline and used for fermenting livestock and poultry feces to produce biogas, wherein the biogas fermentor includes a tank body, an insulating layer provided on an outer side of the tank body, a heating device buried in the insulating layer, an agitating device provided at the lower half portion of the tank body, and a clapboard provided at the upper portion of the tank body and dividing an internal space of the tank body into a main chamber and an auxiliary chamber; the heating device is a warming pipe specifically; upper portions of the auxiliary chamber and the main chamber are in a communicated state and meanwhile lower portions are separated by the clapboard; a biogas residue outlet A is formed in the bottom of the auxiliary chamber, and a biogas slurry outlet is formed in a side wall of the auxiliary chamber; the agitating device is capable of agitating reactants in the main chamber intensively when being started; a feeding hole is formed in the other side, opposite to the agitating device, of the tank body, and a biogas opening and a biogas residue outlet B are respectively formed in the top and the bottom of the tank body; in the prior art, a biogas fermentor has many types of forms, and herein, we adopt an improved completely mixed type reactor, one of disadvantages of conventional completely mixed type reactors is that some hard-to-decompose matters may form floating shells, finally resulting in reduction of fermentation efficiency, and therefore, according to the invention, functional partition is performed on an internal space of a tank body by utilizing a clapboard to avoid the problem, the clapboard is provided on an upper portion of the tank body and divides the internal space of the tank body into a main chamber and an auxiliary chamber, upper portions of the auxiliary chamber and the main chamber are in a communicated state and meanwhile lower portions are separated by the clapboard, the space of the main chamber is relatively large, is a main occurrence site of a fermentation process, and has some similarities with a CSTR internal structure of the prior art, while the auxiliary chamber is a main improved point and communicates with the top of the main chamber, and liquid in the main chamber will overflow into the auxiliary chamber when reaching a certain height, so as to avoid accumulation of scales and increase reaction time of reactants; a biogas residue outlet A is formed in the bottom of the auxiliary chamber and used for discharging biogas residue in regular time, a biogas slurry outlet is formed in a side wall of the auxiliary chamber and used for leading out fermented biogas slurry; the agitating device is provided at a lower portion of the tank body, and is capable of agitating reactants in the main chamber intensively when being started, so as to realize mixing of anaerobic bacteria with reactants; a feeding hole is formed in the other side, opposite to the agitating device, of the tank body, with such design, reactants are agitated intensively as long as entering the tank body, and are gradually removed along with elevation of a liquid level, so that reactants ferment sufficiently, and a disadvantage in the prior art that reactants flow out therewith after flowing into the tank body is avoided, and a biogas opening and a biogas residue outlet B are respectively formed in the top and the bottom of the tank body and are respectively used for conveying biogas and biogas residue; biogas residue and biogas slurry may be recycled directly, and may be discharged after further treatment; in a fermentation process, certain control needs to be performed on temperature in order to cause anaerobic bacteria to reach a suitable working environment, meanwhile, a certain amount of heat release occurs in a fermentation process, therefore, temperature control may be divided into two aspects of heat preservation and heating, in order to save overall cost and space, the invention adopts a design of integration of a warming pipe and an insulating layer, the heating device includes a warming pipe buried in the insulating layer and realizes heating for the tank body via the warming pipe, here, a specific warming principle of the heating pipe may adopt the prior art, such as aqueous medium warming and electrical heated tube warming;

a biogas purifying device connected with the biogas opening by a pipeline and used for removing oil, dust and particle impurities in biogas; biogas produced by directly fermentation of anaerobic bacteria cannot be directly applied or stored, and further treatment needs to be performed on oil and dust therein, so as to prevent blockage of transportation pipelines;

a biogas refining device connected with the biogas purifying device by a pipeline and used for refining biogas, wherein the biogas refining device includes at least one biogas membrane treatment device, the biogas membrane treatment device includes a hollow fibrous membrane in the shape of a wavy line; a biogas inlet, a biogas outlet and an impurity gas outlet are respectively formed in the bottom, the top and the side face of the biogas membrane treatment device; according to the invention, a membrane treatment process is utilized to remove $H_2O$, $H_2S$, $CO_2$, CO and the like synchronously, so as to produce biogas with high methane content, and then functional efficiency is obviously increased in subsequent application;

a biogas compressor connected with a gas outlet of the biogas refining device and used for compressing biogas, and a biogas storage tank connected with the biogas compressor and used for storing biogas, each of the above-mentioned pipelines is provided with a power supply or power device and a valve for conveying a target object from a last structure to a next structure.

Preferably, the agitating device is in a horizontal state, and includes a frame agitator, an inside agitator provided in the frame agitator, a main motor used for driving the frame agitator, a shaft motor used for driving the inside agitator and a gear motor, wherein the inside agitator is one of the followings: an inclined-blade dual-blade agitator, a straight-blade turbine agitator, and a six-inclined-blade disk turbo type agitator;

Illustration: a combined agitating device is adopted in order to realize fermentation and reaction of high-thickness reactants, and the whole combined agitating device is formed by combination of a frame agitator and a blade type agitating head.

Preferably, the clapboard at least includes one section of inclined plate, an included angle between the inclined plate and the horizontal plane being 30-60° or 120-150°, and a super-hydrophobic coating being provided on the surface of the inclined plate;

Illustration: an inclined plate is convenient for inflowing fermented liquid to stay quickly, especially some scums, so as to prevent scums from adhering to the wall.

Preferably, the device also includes:

a settling pond connected with the biogas slurry outlet by a pipeline, wherein a biogas residue outlet C is formed in the bottom of the settling pond;

an MBR treating pond connected with the settling pond by a pipeline, wherein the MBR treating pond is internally provided with at least one MBR plate type membrane, an agitator, an aerator pipe and activated sludge; and a sludge thickener, including a main body, a sludge inlet, a water outlet, and a sludge outlet, wherein the biogas residue outlet A, the biogas residue outlet B and the biogas residue outlet C are all connected to the sludge inlet by pipelines, and the water outlet is connected to the MBR treating pond by a pipeline;

Illustration: fermented biogas slurry and biogas residue still contain a considerable quantity of pollutants, which cannot be directly discharged, wherein biogas slurry is water soluble matter after biogas fermentation, reserves rich amino acid, hydrolytic enzyme, auxin, matters and factors having an inhibiting effect for plant diseases and insect pests, as well as elements such as nitrogen, phosphorus and potassium, and may be taken as quick-acting fertilizer, while biogas residue is semisolid matter left by biogas fermentation, contains rich organic matters, humic acid, amino acid, nitrogen, phosphorus and potassium and the like, and may be taken as a sustained or controlled release fertilizer or a soil conditioner; as for non mixed-mode farms or plantations, biogas slurry or biogas residue cannot be directly recycled, therefore, a settling pond, an MBR treating pond and a sludge thickener may be provided to treat biogas slurry and biogas residue and then discharge;

because biogas slurry discharged by an improved CSTR contains a considerable quantity of suspended solids, MBR needs to be used for sewage treatment after settling, a settling pond is connected with a biogas slurry outlet by a pipeline, a biogas residue outlet C is formed in the bottom of the settling pond, settled supernatant of biogas slurry enters an MBR treating pond to be treated and then is discharged by reaching the standard, sludge thickening is performed on the biogas residue and the former biogas residue discharged from the biogas residue outlet A and the biogas residue outlet B together; the MBR treating pond is connected with the settling pond by a pipeline, and is internally provided with at least one MBR plate type membrane, an agitator, an aerator pipe and activated sludge, sewage may be discharged by reaching the standard after being treated by the MBR treating pond; the sludge thickener includes a main body, a sludge inlet, a water outlet, and a sludge outlet, wherein the biogas residue outlet A, the biogas residue outlet B and the biogas residue outlet C are all connected to the sludge inlet by pipelines, so that sludge is discharged to the outside or recycled after being concentrated, and the water outlet is connected to the MBR treating pond by a pipeline, so that sewage is discharged after being treated, more preferably, the material of the hollow fibrous membrane is macromolecule polyimide; a CS elastic hollow fibrous membrane is taken as a membrane of the MBR plate type membrane; and the material of the insulating layer is polystyrene rock wool for heat preservation;

Illustration: macromolecule polyimide hollow fibrous membrane is long in service life, compact in structure and safe to use, and separation efficiency reaches up to 95%; and CS elastic hollow fibrous membrane is excellent in physical properties such as surface hydrophilicity, non-polarity, mechanical strength, elasticity and toughness, and is long in service life.

Preferably, a second biogas compressor is further provided on a pipeline for connecting the biogas purifying device to the biogas opening, wherein the biogas purifying device includes an oil removal tank, a water removal tank and a particle filtering tank which are connected end to end in sequence;

The function of the second compressor is that compressed biogas may pass the biogas purifying device automatically due to the problem of internal pressure, and additional arrangement of a delivery pump is not needed.

Compared with the prior art, the invention has the following beneficial effects:

(1) a baffle is utilized to divide the interior of a tank body of CSTR, so as to form a main reaction chamber and an auxiliary reaction chamber communicated in upper portions, so that reactants flow into the auxiliary reaction chamber only after entering the main reaction chamber from a relatively low feeding hole and then reaching a high position of a liquid level, and then extension of fermentation time is realized, a disadvantage that reaction raw material just entering CSTR is removed therewith is avoided, and fermentation efficiency is increased;

(2) in the main reaction chamber, scales formed at the top will flow into the auxiliary reaction chamber along with liquid, so that the interior of the main reaction chamber keeps a liquid state all the time, and sealing and reduction of quantity of anaerobic bacteria are avoided;

(3) biogas refinement is performed by membrane separation, so that biogas with high methane content is obtained, and the biogas may reach a quality equal to that of natural gas, separated CO2 may be recycled, meanwhile, absorption of $H_2S$, CO and $H_2O$ may be realized synchronously by membrane separation, and independent arrangement of an acid absorption tower is not needed, so that cost is lowered;

(4) a frame agitator is combined with an agitating head with high agitating speed, so that high-efficiency agitating of high-thickness feces reactants is realized, and feces reactants ferment uniformly; and (5) due to the arrangement of a biogas compressor, subsequent treatment and separation may be performed by using pressure of compressed biogas as driving force, so as to save energy.

Figure 1:
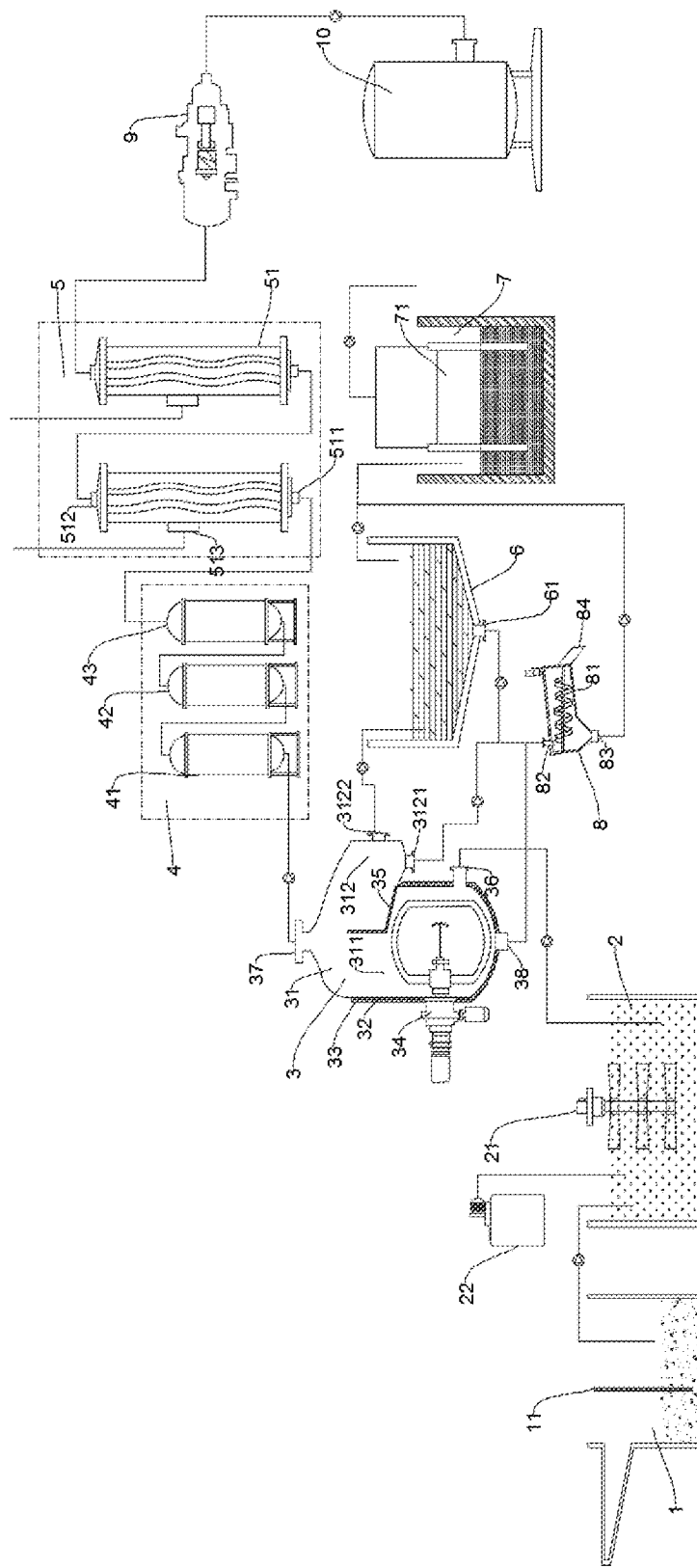
FIG. 1 is a schematic structure diagram of embodiment 2 of the invention.
Figure 2:
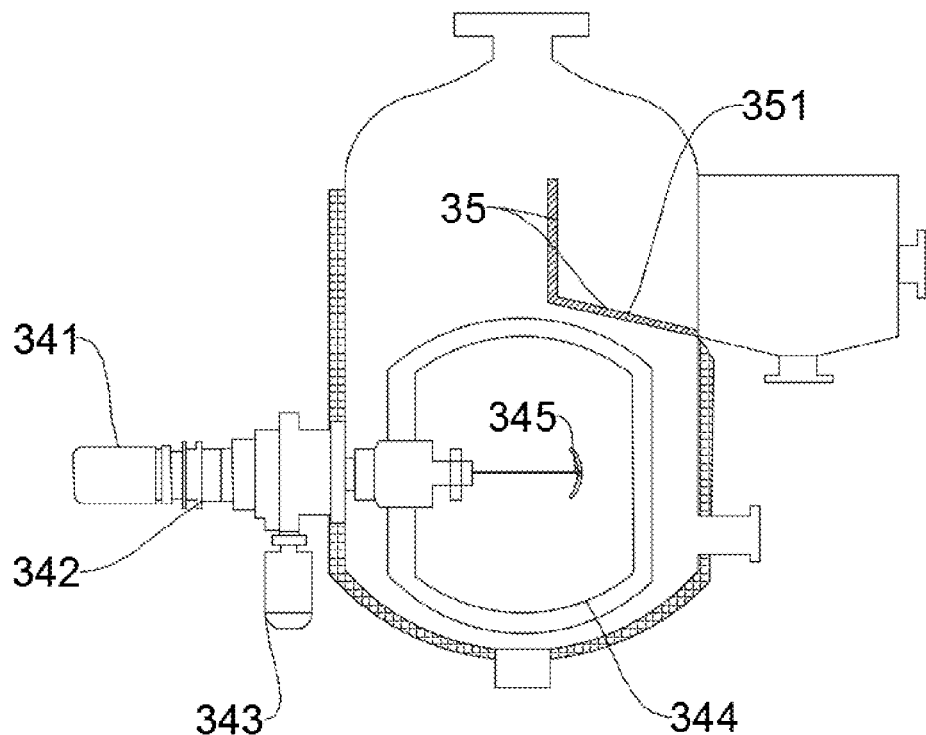
FIG. 2 is a structure diagram of an agitating device of the invention.

In the drawings, 1-feces collecting pond, 11-grids; 2-acidifying pond, 21-agitator, 22-automatic doser or dosing device; 3-biogas fermenting pond, 31-tank body, 311-main chamber, 312-auxiliary chamber, 3121-biogas residue outlet A, 3122-biogas slurry outlet, 32-insulating layer, 33-heating device, 34-agitating device, 341-main motor, 342-gear motor, 343-shaft motor, 344-frame agitator, 345-inside agitator, 35-clapboard, 351-inclined plate, 36-feeding hole, 37-biogas opening, 38-biogas residue outlet B; 4-biogas purifying device, 41-oil removal tank, 42-water removal tank, 43-particle filtering tank; 5-biogas refining device, 51-biogas membrane treatment device, 511-biogas inlet, 512-biogas outlet, 513-impurity gas outlet; 6-settling pond, 61-biogas residue outlet C; 7-MBR treating pond, 71-MBR plate type membrane; 8-sludge thickener, 81-main body, 82-sludge inlet, 83-water outlet, 84-sludge outlet; 9-biogas compressor; 10-biogas storage tank.

DESCRIPTION OF THE EMBODIMENTS

The following clearly and completely describes the technical solutions in the embodiments of the present invention with reference to the accompanying drawings in the embodiments of the present invention. Apparently, the described embodiments are some of the embodiments of the present invention rather than all of the embodiments. All other embodiments obtained by a person of ordinary skill in the art based on the embodiments of the present invention without creative efforts shall fall within the protection scope of the present disclosure.

Embodiment 1

Engineering environment: a large-scale chicken farm, with daily feces production of 4.32 tons, near to a fruit tree culture area.

Figure 3:
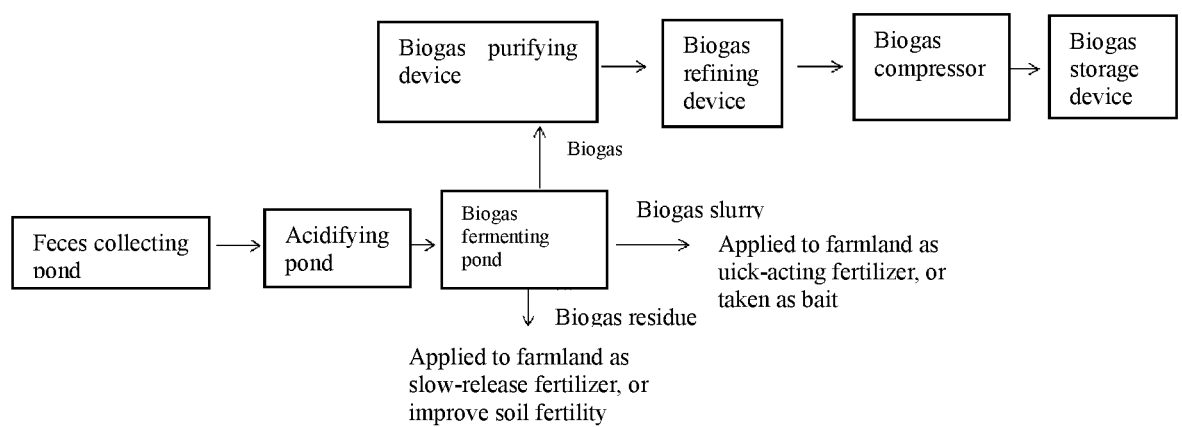
FIG. 3 is a process flow diagram of embodiment 1 of the invention.

A device for producing biogas with high methane content by utilizing livestock and poultry feces is designed aiming at the environment, as shown in FIG. 3, comprising a feces collecting pond 1, an acidifying pond 2, a biogas fermentor 3, a biogas purifying device 4, a biogas refining device 5, a biogas compressor 9 and a biogas storage tank 10, because internal utilization of biogas slurry and biogas residue may be realized in the present embodiment, additional arrangement of a treatment device is not needed;

Pretreatment Unit feces collecting pond 1: design volume 24 $m^3$;

the feces collecting pond 1 is used for collecting livestock and poultry feces in a unified mode, a collecting pipeline is provided in the bottom of a livestock and poultry captive breeding area, so that feces of livestock and poultry and flushing sewage are automatically collected to the feces collecting pond 1 via inclined pipelines, grids 11 are provided in the feces collecting pond 1 and used for intercepting large-size wastes, so as to prevent blockage of pipelines in a transportation process;

acidifying pond 2: design volume 6.6 $m^3$;

the acidifying pond 2 is used for acidifying macrofibers in livestock and poultry feces to be simple organic matters to be convenient for subsequent anaerobic bacteria treatment, the acidifying pond 2 is internally provided with a propelling type agitator 21, and externally provided with an automatic doser or dosing device 22, meanwhile, the acidifying pond 2 regulates feces to a proper viscosity to enter subsequent fermentation;

Fermenting Unit an improved CSTR reactor is adopted as a biogas fermentor 3: design volume 125 $m^3$;

the biogas fermentor 3 is used for fermenting organic matters in feces by utilizing anaerobic bacteria so as to obtain biogas; a specific structure includes a tank body 31, an insulating layer 32, a heating device 33, an agitating device 34 and a clapboard 35, wherein the insulating layer 32 is provided on the outer side of the tank body 31;

in a fermentation process, in order to cause anaerobic bacteria to reach a suitable working environment, the temperature needs to be kept at 35-58 DEG C, meanwhile, a certain amount of heat release occurs in a fermentation process, therefore, temperature control may be divided into two aspects of heat preservation and heating, in order to save overall cost and space, the invention adopts a design of integration of a warming pipe and an insulating layer, the heating device 33 includes a warming pipe buried in the insulating layer 32 and realizes heating for the tank body 31 via the warming pipe, here, a specific warming principle of the heating pipe may be aqueous medium warming;

The biggest disadvantage of CSTR is that some hard-to-decompose matters may form floating shells, finally resulting in reduction of fermentation efficiency, finally resulting in reduction of fermentation efficiency, and therefore, according to the invention, functional partition is performed on an internal space of a tank body 31 by utilizing a clapboard 35 to avoid the problem, the clapboard 35 is provided on an upper portion of the tank body 31 and divides the internal space of the tank body 31 into a main chamber 311 and an auxiliary chamber 312, upper portions of the auxiliary chamber 312 and the main chamber 311 are in a communicated state and meanwhile lower portions are separated by the clapboard 35, the space of the main chamber 311 is relatively large, is a main occurrence site of a fermentation process, and has some similarities with a CSTR internal structure of the prior art, while the auxiliary chamber 312 is a main improved point and communicates with the top of the main chamber 312, and liquid in the main chamber 311 will overflow into the auxiliary chamber 312 when reaching a certain height, so as to avoid accumulation of scales and increase reaction time of reactants; a biogas residue outlet A 3121 is formed in the bottom of the auxiliary chamber 312 and used for discharging biogas residue in regular time, a biogas slurry outlet 3122 is formed in a side wall of the auxiliary chamber 312 and used for leading out fermented biogas slurry; the agitating device 34 is provided at a lower portion of the tank body 31, and is capable of agitating reactants in the main chamber 311 intensively when being started, so as to realize mixing of anaerobic bacteria with reactants;

treatment capacity of the tank body in the present embodiment is relatively small, and a commercially available frame agitator may be adopted as the agitating device 34.

A feeding hole 36 is formed in the other side, opposite to the agitating device 34, of the tank body 31, with such design, reactants are agitated intensively as long as entering the tank body, and are gradually removed along with elevation of a liquid level, so that reactants ferment sufficiently, and a disadvantage in the prior art that reactants flow out therewith after flowing into the tank body is avoided, and a biogas opening 37 and a biogas residue outlet B 38 are respectively formed in the top and the bottom of the tank body and are respectively used for conveying biogas and biogas residue;

wherein biogas enters a subsequent treatment unit, biogas residue is applied to the farmland as a solid organic fertilizer, and biogas slurry may be applied to a farmland or an orchard.

Biogas Purifying Unit oil removal tank 41: model number MJQF DN 25-DN1000 used for removing dust in biogas;

water removal tank 42: model number MQF DN25-DN1000 used for removing dust in biogas;

particle filtering tank 43: model number Environtec G used for removing particles in biogas;

Biogas Refining Unit biogas refining device 5: the biogas refining device 5 includes two biogas membrane treatment devices 51, material of the biogas membrane treatment devices 51 is macromolecule polyimide, which is long in service life, compact in structure and safe to use, and separation efficiency reaches up to 95%; a biogas inlet 511, a biogas outlet 512 and an impurity gas outlet 513 are respectively formed in the bottom, the top and the side face each of the biogas membrane treatment devices 51;

commercially available polyimide membrane separators of UBE company are adopted as the biogas membrane treatment devices 51; purified biogas still has a high content of carbon dioxide and may reach the quality of natural gas after being further refined, so that combustion efficiency is increased and combustion pollutants are reduced, meanwhile, $H_2O$, $H_2S$, $CO_2$, $CO$ and the like are removed, biogas with high methane content is produced, and functional efficiency is obviously increased in subsequent application.

Biogas Storage Unit

Biogas compressor 9: model number VW-3/30 used for pressurizing biogas for storage;

biogas storage tank 10: design volume 42 $m^3$;

used for storing biogas to be distributed to surrounding residents for use.

According to the engineering theory, daily feces treatment capacity is 5.6 t, daily biogas production capacity is 120 $m^3$, daily biogas residue production capacity is 0.0125 t, biogas slurry production capacity is 3.256 t, and the methane content of the produced biogas reaches up to 67-72%, which is close to the quality of natural gas.

Embodiment 2

Engineering environment: a large-scale livestock farm, with daily feces production of 7.32 tons, near to a farm.

A device for producing biogas with high methane content by utilizing livestock and poultry feces is designed aiming at the environment, as shown in FIG. 3, comprising a feces collecting pond 1, an acidifying pond 2, a biogas fermentor 3, a biogas purifying device 4, a biogas refining device 5, a biogas compressor 9 and a biogas storage tank 10, because internal utilization of biogas slurry and biogas residue may be realized in the present embodiment, additional arrangement of a treatment device is not needed;

Pretreatment Unit feces collecting pond 1: design volume 24 $m^3$;

the feces collecting pond 1 is used for collecting livestock and poultry feces in a unified mode, a collecting pipeline is provided in the bottom of a livestock and poultry captive breeding area, so that feces of livestock and poultry and flushing sewage are automatically collected to the feces collecting pond 1 via inclined pipelines, grids 11 are provided in the feces collecting pond 1 and used for intercepting large-size wastes, so as to prevent blockage of pipelines in a transportation process;

acidifying pond 2: design volume 4.3 $m^3$;

the acidifying pond 2 is used for acidifying macrofibers in livestock and poultry feces to be simple organic matters to be convenient for subsequent anaerobic bacteria treatment, the acidifying pond 2 is internally provided with a propelling type agitator 21, and externally provided with an automatic doser or dosing device 22, meanwhile, the acidifying pond 2 regulates feces to a proper viscosity to enter subsequent fermentation;

Fermenting Unit an improved CSTR reactor is adopted as a biogas fermentor 3: design volume 186 $m^3$;

the structure of the biogas fermentor 3 of the present embodiment is basically the same as that of the biogas fermentor in embodiment 1, however, because the viscosity of feces of the present embodiment is relatively high, an inclined section 351 is designed for the clapboard 35, and an included angle between the inclined section 351 and the horizontal plane is 145°, so as to prevent feces from adhering to the wall.

Biogas Purifying Unit

Similar to embodiment 1.

Biogas Refining Unit

Similar to embodiment 1.

Biogas Storage Unit

Biogas compressor 9: model number VW-3/30 used for pressurizing biogas for storage;

biogas storage tank 10: design volume 40 m$^3$;

used for storing biogas to be distributed to surrounding residents for use.

According to the engineering theory, daily feces treatment capacity is 9 t, daily biogas production capacity is 100 m$^3$, daily biogas residue production capacity is 0.062 t, biogas slurry production capacity is 5.65 t, and the methane content of the produced biogas reaches up to 67-72%, which is close to the quality of natural gas.

Embodiment 3

Engineering environment: a large-scale breeding-planting comprehensive agricultural and grazing garden, with daily feces production of 12.32 tons.

A device for producing biogas with high methane content by utilizing livestock and poultry feces is designed aiming at the environment, as shown in FIG. 3, comprising a feces collecting pond 1, an acidifying pond 2, a biogas fermentor 3, a biogas purifying device 4, a biogas refining device 5, a biogas compressor 9 and a biogas storage tank 10, because internal utilization of biogas slurry and biogas residue may be realized in the present embodiment, additional arrangement of a treatment device is not needed;

Pretreatment Unit feces collecting pond 1: design volume 42 m$^3$;

the feces collecting pond 1 is used for collecting livestock and poultry feces in a unified mode, a collecting pipeline is provided in the bottom of a livestock and poultry captive breeding area, so that feces of livestock and poultry and flushing sewage are automatically collected to the feces collecting pond 1 via inclined pipelines, grids 11 are provided in the feces collecting pond 1 and used for intercepting large-size wastes, so as to prevent blockage of pipelines in a transportation process;

acidifying pond 2: design volume 18.7 m$^3$;

the acidifying pond 2 is used for acidifying macrofibers in livestock and poultry feces to be simple organic matters to be convenient for subsequent anaerobic bacteria treatment, the acidifying pond 2 is internally provided with a propelling type agitator 21, and externally provided with an automatic doser or dosing device 22, meanwhile, the acidifying pond 2 regulates feces to a proper viscosity to enter subsequent fermentation;

Fermenting Unit an improved CSTR reactor is adopted as a biogas fermentor 3: design volume 368 m$^3$;

the composition and structure of the biogas fermentor 3 of the present embodiment are basically the same as those of the biogas fermentor in embodiment 2, however, because the feces amount needing to be treated in the present embodiment is large, a combined agitating device is adopted, the whole combined agitating device is formed by combination of a frame agitator and an inclined-blade dual-blade agitator, the whole device is in a horizontal state, and includes a main motor 341, a gear motor 342, a shaft motor 343, a frame agitator 344 and an inside agitator 345, the inside agitator 345 is provided in the frame agitator 344, and the main motor 341 and the shaft motor 343 are respectively used for driving the frame agitator 344 and the inside agitator 345.

Biogas Purifying Unit

Similar to embodiment 1.

Biogas Refining Unit

Similar to embodiment 1.

Biogas Storage Unit

Biogas compressor 9: model number VW-3/30 used for pressurizing biogas for storage;

biogas storage tank 10: design volume 120 m$^3$;

used for storing biogas to be distributed to surrounding residents and livestock farms to be used for supplying water and power.

According to the engineering theory, daily feces treatment capacity is 15 t, daily biogas production capacity is 160 m$^3$, daily biogas residue production capacity is 0.075 t, biogas slurry production capacity is 8.39 t, and the methane content of the produced biogas reaches up to 70-74%, which is close to the quality of natural gas.

Embodiment 4

Engineering environment: a hybrid agricultural base, with 2000 live pigs and daily feces production of 8.67 tons, cultivating 200 mu dry farming field, near to a residential district.

A device for producing biogas with high methane content by utilizing livestock and poultry feces is designed aiming at the environment, as shown in FIG. 3, comprising a feces collecting pond 1, an acidifying pond 2, a biogas fermentor 3, a biogas purifying device 4, a biogas refining device 5, a biogas compressor 9 and a biogas storage tank 10, because internal utilization of biogas slurry and biogas residue may be realized in the present embodiment, additional arrangement of a treatment device is not needed;

Pretreatment Unit feces collecting pond 1: design volume 30 m$^3$;

the feces collecting pond 1 is used for collecting livestock and poultry feces in a unified mode, a collecting pipeline is provided in the bottom of a livestock and poultry captive breeding area, so that feces of livestock and poultry and flushing sewage are automatically collected to the feces collecting pond 1 via inclined pipelines, grids 11 are provided in the feces collecting pond 1 and used for intercepting large-size wastes, so as to prevent blockage of pipelines in a transportation process;

acidifying pond 2: design volume 17.6 m$^3$;

the acidifying pond 2 is used for acidifying macrofibers in livestock and poultry feces to be simple organic matters to be convenient for subsequent anaerobic bacteria treatment, the acidifying pond 2 is internally provided with a propelling type agitator 21, and externally provided with an automatic doser or dosing device 22, meanwhile, the acidifying pond 2 regulates feces to a proper viscosity to enter subsequent fermentation;

Fermenting Unit an improved CSTR reactor is adopted as a biogas fermentor 3: design volume 324 m$^3$;

the structure and composition of the biogas fermentor 3 in the present embodiment are the same as those in embodiment 3.

Biogas Purifying Unit

Similar to embodiment 1.

Biogas Refining Unit biogas refining device 5: the biogas refining device 5 includes three biogas membrane treatment devices 51, material of the biogas membrane treatment devices 51 is macromolecule polyimide, which is long in service life, compact in structure and safe to use, and separation efficiency reaches up to 95%; a biogas inlet 511, a biogas outlet 512 and an impurity gas outlet 513 are respectively formed in the bottom, the top and the side face each of the biogas membrane treatment devices 51;

a customized form is adopted for the biogas membrane treatment devices 51, and the hollow fibrous membrane is customized as a bent wavy form, so as to increase contact area with biogas, and increase refining efficiency.

Biogas Storage Unit

Biogas compressor 9: model number VW-3/30 used for pressurizing biogas for storage;

biogas storage tank 10: design volume 96 m$^3$;

used for storing biogas to be distributed to surrounding residents for use.

According to the engineering theory, daily feces treatment capacity is 10 t, daily biogas production capacity is 200 m$^3$, daily biogas residue production capacity is 0.0675 t, biogas slurry production capacity is 8.279 t, and the methane content of the produced biogas reaches up to 70-82%, which is close to the quality of natural gas.

Embodiment 5

Engineering environment: a dairy farm, with 2000 cows in total; without residential districts and farmlands nearby.

Figure 4:
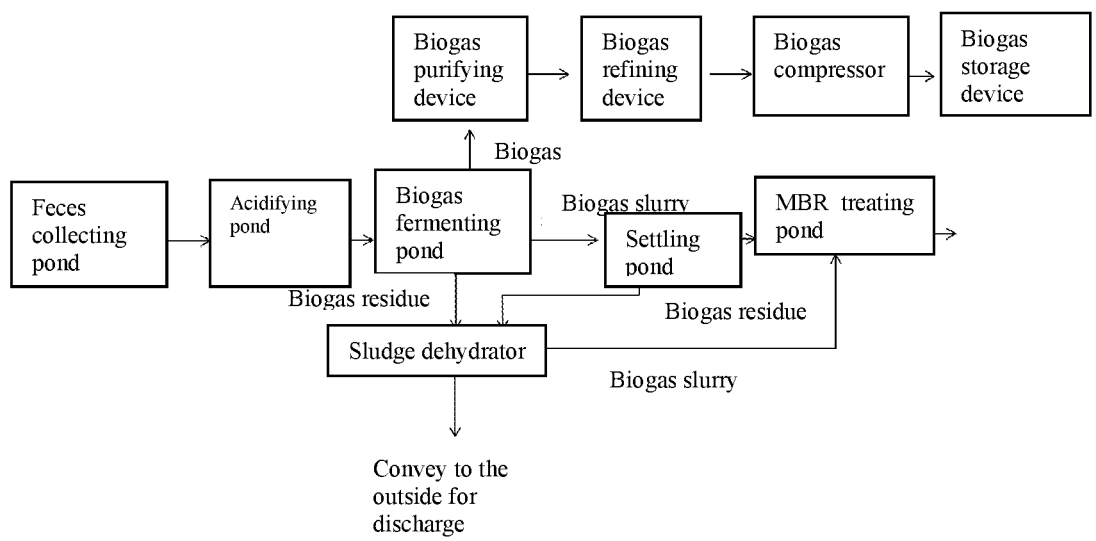
FIG. 4 is a process flow diagram of embodiment 2 of the invention.

A device for producing biogas with high methane content by utilizing livestock and poultry feces is designed aiming at the environment, as shown in FIG. 4, comprising a feces collecting pond 1, an acidifying pond 2, a biogas fermentor 3, a biogas purifying device 4, a biogas refining device 5, a settling pond 6, an MBR treating pond 7, a sludge thickener 8, a biogas compressor 9 and a biogas storage tank 10, the farm only needs to recycle biogas residues and expects to discharge biogas slurry after treatment, as a result, a biogas slurry treatment unit is additionally provided;

Pretreatment Unit feces collecting pond 1: design volume 36 m$^3$;

the feces collecting pond 1 is used for collecting livestock and poultry feces in a unified mode, a collecting pipeline is provided in the bottom of a livestock and poultry captive breeding area, so that feces of livestock and poultry and flushing sewage are automatically collected to the feces collecting pond 1 via inclined pipelines, grids 11 are provided in the feces collecting pond 1 and used for intercepting large-size wastes, so as to prevent blockage of pipelines in a transportation process;

acidifying pond 2: design volume 16 m$^3$;

the acidifying pond 2 is used for acidifying macrofibers in livestock and poultry feces to be simple organic matters to be convenient for subsequent anaerobic bacteria treatment, the acidifying pond 2 is internally provided with a propelling type agitator 21, and externally provided with an automatic doser or dosing device 22, meanwhile, the acidifying pond 2 regulates feces to a proper viscosity to enter subsequent fermentation;

Fermenting Unit an improved CSTR reactor is adopted as a biogas fermentor 3: design volume 348 m$^3$;

the structure and composition of the biogas fermentor 3 in the present embodiment are the same as those in embodiment 3.

Biogas Purifying Unit

Similar to embodiment 1.

Biogas Refining Unit

Similar to embodiment 4.

Biogas Storage Unit

Biogas compressor 9: model number VW-3/30 used for pressurizing biogas for storage;

biogas storage tank 10: design volume 96 m$^3$;

used for storing biogas to be distributed to surrounding residents for use.

According to the engineering theory, daily feces treatment capacity is 10 t, daily biogas production capacity is 200 m$^3$, daily biogas residue production capacity is 0.0675 t, biogas slurry production capacity is 8.279 t, and the methane content of the produced biogas reaches up to 70-82%, which is close to the quality of natural gas.

Biogas Slurry Treatment Unit settling pond 6: design volume 21 m$^3$;

the settling pond 6 is used for performing further settling treatment on biogas slurry, wherein supernatant enters an MBR treating pond and then is discharged; and precipitates enter to be utilized together with biogas residues;

MBR treating pond 7: internally provided with a PVDF composite plate type membrane;

the MBR treating pond 7 is used for treating biogas slurry and discharging by reaching the standard, and further includes an agitator, an aerator pipe and activated sludge.

Embodiment 6

Engineering environment: a cow and sheep hybrid farm, with 1000 cows and 800 sheep in total, and a number of chickens and ducks; without residential districts and farmlands nearby.

A device for producing biogas with high methane content by utilizing livestock and poultry feces is designed aiming at the environment, as shown in FIG. 4, comprising a feces collecting pond 1, an acidifying pond 2, a biogas fermentor 3, a biogas purifying device 4, a biogas refining device 5, a settling pond 6, an MBR treating pond 7, a sludge thickener 8, a biogas compressor 9 and a biogas storage tank 10, because a planting region is absent near the farm, both biogas slurry and biogas residues need to be discharged after being treated, as a result, a biogas slurry treatment unit and a biogas residue treatment unit are additionally provided.

Pretreatment Unit feces collecting pond 1: design volume 66 m$^3$;

the feces collecting pond 1 is used for collecting livestock and poultry feces in a unified mode, a collecting pipeline is provided in the bottom of a livestock and poultry captive breeding area, so that feces of livestock and poultry and flushing sewage are automatically collected to the feces collecting pond 1 via inclined pipelines, grids 11 are provided in the feces collecting pond 1 and used for intercepting large-size wastes, so as to prevent blockage of pipelines in a transportation process;

acidifying pond 2: design volume 24.6 m$^3$;

the acidifying pond 2 is used for acidifying macrofibers in livestock and poultry feces to be simple organic matters to be convenient for subsequent anaerobic bacteria treatment, the acidifying pond 2 is internally provided with a propelling type agitator 21, and externally provided with an automatic doser or dosing device 22, meanwhile, the acidifying pond 2 regulates feces to a proper viscosity to enter subsequent fermentation;

Fermenting Unit an improved CSTR reactor is adopted as a biogas fermentor 3: design volume 314 m$^3$;

the structure and composition of the biogas fermentor 3 in the present embodiment are the same as those in embodiment 3.

Biogas Purifying Unit

Similar to embodiment 1.

Biogas Refining Unit

Similar to embodiment 4.

Biogas Storage Unit

Biogas compressor 9: model number VW-3/30 used for pressurizing biogas for storage;

biogas storage tank 10: design volume 140 m$^3$;

used for storing biogas to be distributed to surrounding residents for use.

According to the engineering theory, daily feces treatment capacity is 14 t, daily biogas production capacity is 200 m$^3$, daily biogas residue production capacity is 0.0588 t, biogas slurry production capacity is 7.689 t, and the methane content of the produced biogas reaches up to 82-85%, which is close to the quality of natural gas.

Biogas Slurry Treatment Unit settling pond 6: design volume 25 m$^3$;

the settling pond 6 is used for performing further settling treatment on biogas slurry, wherein supernatant enters an MBR treating pond and then is discharged; and precipitates enter to be utilized together with biogas residues;

MBR treating pond 7: internally provided with a PVDF composite plate type membrane;

the MBR treating pond 7 is used for treating biogas slurry and discharging by reaching the standard, and further includes an agitator, an aerator pipe and activated sludge.

sludge thickener 8: with model number of FDY high-concentration thickener;

the sludge thickener 8 is used for concentrating biogas residues and then conveying to the outside, and includes a main body 81, a sludge inlet 82, a water outlet 83 and a sludge outlet 84, the biogas residue outlet A 3121, the biogas residue outlet B 38 and the biogas residue outlet C 61 are all connected to the sludge inlet 82 by pipelines; and the water outlet 83 is connected to the MBR treating pond (7) by a pipeline.

What is claimed is:

1. A device for producing biogas with high methane content by utilizing livestock and poultry feces, comprising:
    a feces collecting pond used for collecting livestock and poultry feces in a unified mode, the feces collecting pond being internally provided with grids for filtering feces,
    an acidifying pond connected with the feces collecting pond by a pipeline and used for acidifying livestock and poultry feces, the acidifying pond being internally provided with an agitator, and being externally provided with an automatic doser,
    a biogas fermentor connected with the acidifying pond by a pipeline and used for fermenting livestock and poultry feces to produce biogas, the biogas fermentor comprising a tank body, an insulating layer provided on an outer side of the tank body, a heating device buried in the insulating layer, an agitator provided at the lower half portion of the tank body, and a clapboard provided at the upper portion of the tank body and dividing an internal space of the tank body into a main chamber and an auxiliary chamber; the heating device being a warming pipe specifically; upper portions of the auxiliary chamber and the main chamber being in a communicated state and meanwhile lower portions being separated by the clapboard; a biogas residue outlet A being formed in the bottom of the auxiliary chamber, and a biogas slurry outlet being formed in a side wall of the auxiliary chamber; the agitator being capable of agitating reactants in the main chamber intensively when being started; a feeding hole being formed in the other side, opposite to the agitating device, of the tank body, and a biogas opening and a biogas residue outlet B being respectively formed in the top and the bottom of the tank body,
    a biogas purifier connected with the biogas opening by a pipeline and used for removing oil, dust and particle impurities in biogas,
    a biogas refiner connected with the biogas purifier by a pipeline and used for refining biogas, the biogas refiner comprising at least one biogas membrane treatment device, the biogas membrane treatment device comprising a hollow fibrous membrane in the shape of a wavy line; a biogas inlet, a biogas outlet and an impurity gas outlet being respectively formed in the bottom, the top and the side face of the biogas membrane treatment device,
    a biogas compressor connected with a gas outlet of the biogas refining device and used for compressing biogas, and
    a biogas storage tank connected with the biogas compressor and used for storing biogas,
    each of the above-mentioned pipelines being provided with a power supply and a valve for conveying a target object from a last structure to a next structure.

2. The device for producing biogas with high methane content by utilizing livestock and poultry feces according to claim 1, wherein the agitator is in a horizontal state, and comprises a frame agitator, an inside agitator provided in the frame agitator, a main motor used for driving the frame agitator, a shaft motor used for driving the inside agitator and a gear motor, the inside agitator being one of the followings: an inclined-blade dual-blade agitator, a straight-blade turbine agitator, and a six-inclined-blade disk turbo agitator.

3. The device for producing biogas with high methane content by utilizing livestock and poultry feces according to claim 1, wherein the clapboard at least comprises one section of inclined plate, an included angle between the inclined plate and the horizontal plane being 30-60° or 120-150°, and a super-hydrophobic coating being provided on the surface of the inclined plate.

4. The device for producing biogas with high methane content by utilizing livestock and poultry feces according to claim 1, wherein a second biogas compressor is further provided on a pipeline for connecting the biogas purifying device to the biogas opening, the biogas purifying device comprising an oil removal tank, a water removal tank and a particle filtering tank which are connected end to end in sequence.

* * * * *